(12) United States Patent
Lal et al.

(10) Patent No.: US 10,933,155 B2
(45) Date of Patent: Mar. 2, 2021

(54) VAPOR DISPENSING METHOD AND APPARATUS

(71) Applicants: Ravi G. Lal, Ithaca, NY (US); Amit Lal, Ithaca, NY (US)

(72) Inventors: Ravi G. Lal, Ithaca, NY (US); Amit Lal, Ithaca, NY (US)

(*) Notice: Subject to any disclaimer, the term of this patent is extended or adjusted under 35 U.S.C. 154(b) by 0 days.

(21) Appl. No.: 16/773,347

(22) Filed: Jan. 27, 2020

(65) Prior Publication Data
US 2020/0197557 A1  Jun. 25, 2020

Related U.S. Application Data

(63) Continuation-in-part of application No. 15/108,490, filed as application No. PCT/US2014/070440 on Dec. 16, 2014, now Pat. No. 10,543,292.

(60) Provisional application No. 61/921,192, filed on Dec. 27, 2013.

(51) Int. Cl.
*A61L 9/03* (2006.01)
*A61L 9/12* (2006.01)

(52) U.S. Cl.
CPC .......... *A61L 9/122* (2013.01); *A61L 2209/111* (2013.01)

(58) Field of Classification Search
CPC ... A61L 9/03; A61L 9/12; A61L 9/122; A61L 2209/13
USPC .......................................................... 222/3
See application file for complete search history.

(56) References Cited

U.S. PATENT DOCUMENTS

| 1,747,365 | A | | 2/1930 | Hardinge |
| 5,054,691 | A | * | 10/1991 | Huang ............... F02M 61/1853 239/585.3 |
| 5,233,680 | A | | 8/1993 | Fussell |
| 2004/0195351 | A1 | | 10/2004 | Leonard et al. |
| 2008/0169306 | A1 | | 7/2008 | Bankers et al. |
| 2008/0169354 | A1 | | 7/2008 | Bankers et al. |
| 2008/0311008 | A1 | | 12/2008 | Tranzeat |
| 2009/0008470 | A1 | | 1/2009 | Feuillard et al. |
| 2013/0020729 | A1 | | 1/2013 | Hall |
| 2014/0093224 | A1 | | 4/2014 | Deflorian et al. |
| 2018/0363591 | A1 | * | 12/2018 | Etcheverry ........ F02M 21/0275 |

OTHER PUBLICATIONS

International Search Report and Written Opinion for International Application No. PCT/US2014/070440, International Filing Date Dec. 16, 2014, dated Mar. 17, 2015, 8 pages.

* cited by examiner

*Primary Examiner* — Kevin Joyner
(74) *Attorney, Agent, or Firm* — Bond, Schoeneck & King PLLC; Erin Phillips

(57) ABSTRACT

A method and apparatus for vapor dispensing apparatus is described. The vapor dispensing apparatus includes: a housing defining a chamber having an inner contact surface, wherein the housing further comprises an aperture providing fluid communication between the chamber and an external environment; an evaporable material receptacle movably disposed within the chamber such that a dispensing portion of the receptacle is disposed in contact with at least a portion of the surface; and a motor coupled to the apparatus, configured to move the receptacle.

9 Claims, 18 Drawing Sheets

VAPOR DISPENSING METHOD AND APPARATUS

1. CROSS-REFERENCE TO RELATED APPLICATION

This application is a continuation-in-part of U.S. Non-Provisional application Ser. No. 15/108,490, filed Jun. 27, 2016, which was a U.S. National Stage Application of International Application No. PCT/US14/70440, filed Dec. 16, 2014, which claims the benefit of U.S. Provisional Application No. 61/921,192, filed Dec. 27, 2013, each of which is hereby incorporated by reference in its entirety.

2. FIELD OF INVENTION

Embodiments of the invention generally relate to a vapor delivery device and associated methods and more particularly to a vapor delivery device which dispenses a vapor through diffusion.

3. BACKGROUND

There are different types of liquids—such as aroma therapy solutions and perfumes as well as mosquito repellant liquids, and solids such as waxes and soft plastics that benefit from being vaporized to achieve their desired or intended function and results (e.g., olfactory; repellant, etc.). Methods and apparatus to deliver liquids (and/or solids) through vaporization exist in many forms. These include, but are not limited to, thermal vaporization, compressed gas vaporization, and ultrasonic atomization of liquids.

In the process of thermal vaporization, the liquid is heated to its vaporization temperature. In the case of heat vaporization, the energy required to heat liquids can be substantial and battery powered operation is sometimes not feasible. Furthermore, for multiliquid mixtures such as mixtures of solvents and concentrate perfumes, each component volatilizes at different rates due to different vapor pressures that depend on the chemical constitution of the liquid. This leads to different smells being generated over time compared to the intended olfactory response. Additionally, sometimes the temperature required for thermal vaporization is very high, unsuitable for portable and low-power applications.

In ultrasonic atomization, a liquid is vibrated at sufficiently high velocities and frequencies to cause the liquid to be broken up into droplets due to capillary waves that become sufficiently large. In the ultrasonic method, the liquid needs to be delivered to a high velocity surface requiring high frequency actuators that require special electronics and high degree of control for optimal control. The technique does not work well for high viscosity liquids such as oils, requiring excessive power for vaporization and atomization.

In the case of compressed gas atomization, the liquid is vaporized with the flow of compressed gas stored together with the liquid perfume. The high velocity of the carrier gas with ejected liquid can cause the liquid to be broken up into droplets that eventually vaporize into air. With high compressed gas flow, the high flow rate generally leads to a high audio output that is heard by people around the activated area, drawing attention to the act of spraying. The high velocity of the exiting fluids also can cause the liquid to impact a surface at some distance from the sprayer. Most importantly, the delivery method requires the formation of aerosols that consist of unhealthy chemicals such as benzene, and higher molecular mass organic compounds that can be allergens.

Another form of liquid delivery is accomplished with a 'roll-on' bottle, in which the liquid is applied to the surface of a roller ball coupled to the bottle from within the bottle. As the ball is rolled and contacted with a surface, the liquid is deposited on the surface and absorbed in some cases. Due to the increased surface area, the liquid can vaporize or evaporate at a higher rate compared to when it is inside the bottle. Furthermore, the surface can be at a higher temperature to increase the evaporation rate. Small aplicator $102s$ are used for perfume by applying the roll-on to skin. The higher skin temperature compared to the ambient temperature volatilizes the perfume so that the vapors can reach the olfactory system. The roll-on technique of liquid delivery conventionally requires manual application as well as storage—a person has to actually apply the roll-on by themselves. The roll-on technique has been used for a long period of time and is well established as a way to deliver thick oils and liquids that are very natural without any chemical additives. However, a disadvantage of the roll-on technique is the requirement of manual application. Furthermore, in most applications, the vapor-generated flow cannot be controlled as it is applied to open surfaces.

In view of the foregoing, solution to this and other problems in the art is provided by an automated dispenser and associated method for dispensing a liquid on a contact surface formed within a chamber, there would be benefits outlined below from automating the process and apparatus.

SUMMARY OF THE INVENTION

The present disclosure is directed to inventive methods and apparatus for vapor dispensing. Various embodiments and implementations herein are directed to a vapor dispensing method and apparatus in which an applicator containing a fragrant liquid is pressed against a contact surface within a container to dispense the fragrant liquid. Using the various embodiments and implementations herein, vapor may be dispensed in a controlled fashion with low power, and without using aerosolized compounds. In one exemplary aspect, a vapor dispensing apparatus, includes: a housing defining a chamber having an inner contact surface, wherein the housing further comprises an aperture providing fluid communication between the chamber and an external environment; an evaporable material receptacle movably disposed within the chamber such that a dispensing portion of the receptacle is disposed in contact with at least a portion of the surface; and a motor coupled to the apparatus, configured to move the receptacle.

According to an embodiment, the receptacle further comprises a spherical movable dispensing surface at one end.

According to an embodiment, the liquid is fragrant.

According to another embodiment, an actuator is positioned to draw air through the aperture.

According to another embodiment, a covering is movably disposed within the chamber to cover and seal the aperture.

According to another embodiment, the motor is configured to move the covering.

According to another embodiment, the motor is coupled to the cover by an arm.

According to another embodiment, arm is spring-loaded.

According to another embodiment, a gas sensor is positioned to sense the presence of a vapor within the chamber.

According to another embodiment, a resistive heater positioned to heat at least a portion of the inner contact surface.

According to another embodiment, the motor is actuated by a microcontroller.

According to another embodiment, the microcontroller is configured to actuate the motor at a predetermined time.

According to another embodiment, the motor is actuated by a remote control.

According to another embodiment, the inner contact surface is covered with a rough material.

According to another embodiment, the chamber is cylindrical.

According to another embodiment, the motor moves the receptacle by rotating it.

According to another embodiment, the housing is partially formed by a bottom member, and the motor rotates the receptacle in an arc parallel to the bottom member.

According to another embodiment, the housing is partially formed by a bottom member, and the motor rotates the receptacle in an arc oblique to the bottom member.

According to another embodiment, the receptacle is mounted to a shaft comprising a universal joint, configured such that the receptacle is rotated in an arc not parallel to the ground.

An embodiment of the invention is a method for dispensing a vapor. In an exemplary aspect, the method includes the steps of: providing a substance in at least one of liquid and a solid form in a receptacle disposed in a housing defining a chamber having an internal contact surface; and moving a dispensing portion of the receptacle over an internal contact surface so as to dispense at least a portion of the substance on at least a portion of internal contact surface; and allowing a vapor of the dispensed portion of the substance to escape the housing.

According to an embodiment, the method further comprises the steps of: providing a movably disposed covering within the housing; moving the covering to seal the housing.

According to an embodiment, the method further comprises the step of heating the internal contact surface.

According to another embodiment, the step of moving the receptacle is accomplished by rotating the receptacle in arc.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF NON-LIMITING EXEMPLARY EMBODIMENTS

Non-limiting embodiments of the invention are directed to apparatus and methods for controllably delivering a vapor by controlling the delivery of a liquid or a solid precursor (hereinafter referred to as a 'liquid) to a surface and utilizing at least one of temperature, valving, and air flow to deliver the vapor to a user of the apparatus.

Figure 1:
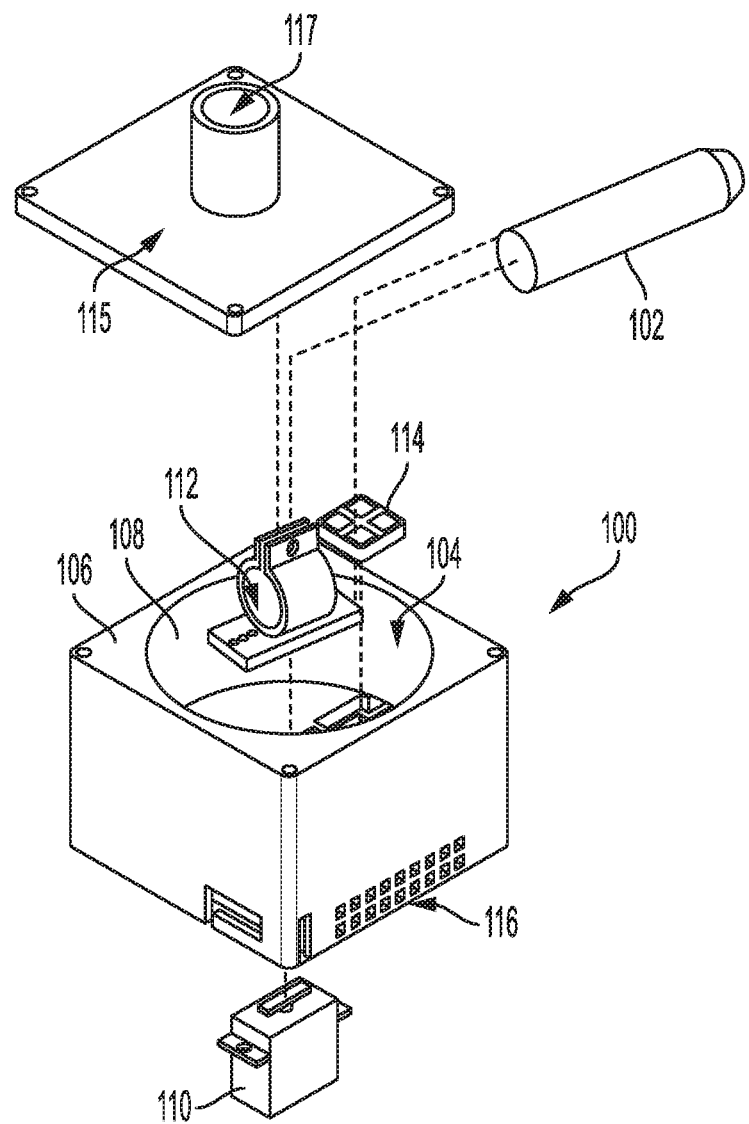
FIG. 1. shows an exploded view of a vapor dispensing apparatus according to an exemplary embodiment of the invention.

Referring now to the figures, wherein like reference numerals refer to like parts throughout, there is shown in FIG. 1, shows a vapor dispensing apparatus 100. In a general non-limiting embodiment, an applicator 102 object held in the center of a chamber 104, defined by a housing 106, and moved over an internal contact surface 108 of the chamber 104 by a motor 110 or, manually by operation of a mechanical mechanism. The applicator 102 may be mounted to the motor 110 by a clamp 112. An actuator that can cause air to circulate through the cavity will pump the vaporized material to be carried outside of the container. An example of such an actuator is a fan 114, as shown in FIG. 1, to blow air throughout the package. In an exemplary embodiment, air will be carried out through an orifice 116. Furthermore, the housing may have a removable cap 117 to contain fumes, and also to provide easy access to the housing internals. Cap 117 may contain a second orifice 115 to vent liquid vapor, or may be completely sealed (see FIG. 3). Finally, housing 116 may further comprise a bottom member 119 to seal the bottom of the bottom of the container.

The applicator 102 can be a roll-on bottle. In this embodiment, the roll-on bottle may dispense liquid when pressure is applied to the roller-ball or, alternatively, it may stop dispensing when pressure is applied to the roller-ball. The applicator 102 can also be a bottle-shaped solid, such as a perfumed wax packaged in a plastic container, or even a crayon shaped device, or a pencil, or a fountain pen. In the preferred embodiment, the applicator 102 is easily removable, such that a user could replace or refill the applicator 102.

The applicator 102 may also have a spring to press the applicator 102 towards the contact surface 108. The applicator 102 may also have an interior wall that is spring-loaded or is mounted to a threaded rod such that turning the rod advances the wall toward the liquid. This may be useful when using solid sources such as wax sticks that will be need to be advanced towards the contact surface 108 as the solid is transferred shortening the stick.

Figure 2:
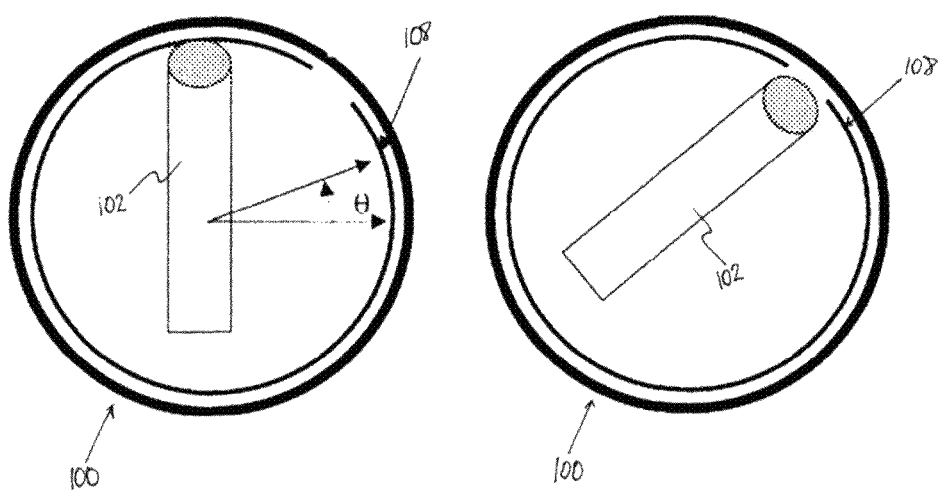
FIG. 2. shows a schematic view of one embodiment of the invention.

In the embodiment, as shown in FIG. 2, the surface 108 onto which the material is applied is circular with its radius varying as a function of theta. The varying radius versus theta would provide a variable contact area between the rotating applicator 102 and the contact surface 108. If the gap is greater than zero then the material will not be transferred to the contact surface 108. When the gap between the applicator 102 and contact surface is zero, the material will be transferred to the contact surface 108. Even in this condition, the force with which the applicator 102 presses onto the contact surface 108 may determine the amount of material transferred to the surface 108. For example in the case of a roller-ball bottle, higher force may result in increased liquid output from the bottle depending on the roller-ball design. In alternative embodiments, perfectly circular, or flat or substantially flat. In this embodiment, the applicator 102 may be in constant contact with the surface during use, or may be manually or mechanically retracted from the surface 108.

Furthermore, in the embodiment, as shown in FIG. 2, the applicator 102 is moved over the surface 108 by rotating the applicator 102. In this embodiment, the contact surface 108 is preferably circular. In an alternative embodiment, the applicator 102 may be drawn over a track, or placed on the end of a rod to be swung in an arc. In these embodiments, the contact surface 108 may preferably be planar or substantially planar.

The contact surface 108 can be mechanically flexible such that the contact force between the applicator 102 and the contact surface 108 can lead to bending of the contact surface. The contact surface 108 can also have areas with holes (lack of contact surface 108 material) such that if the applicator 102 is positioned in these locations, there can be no material transfer. This can be the park position of the contact surface 108. Alternatively, in the embodiment with a roller-ball which ceases to dispense liquid upon the application of pressure on the roller-ball, the applicator 102 may be parked in a position against the contact surface 108, such that the pressure prevents the dispensation of any liquid.

The contact surface 108 can be heated to volatilize the liquid. In one embodiment, this heating can be accomplished by attached resistive heaters on the contact surface 108.

Figure 3:
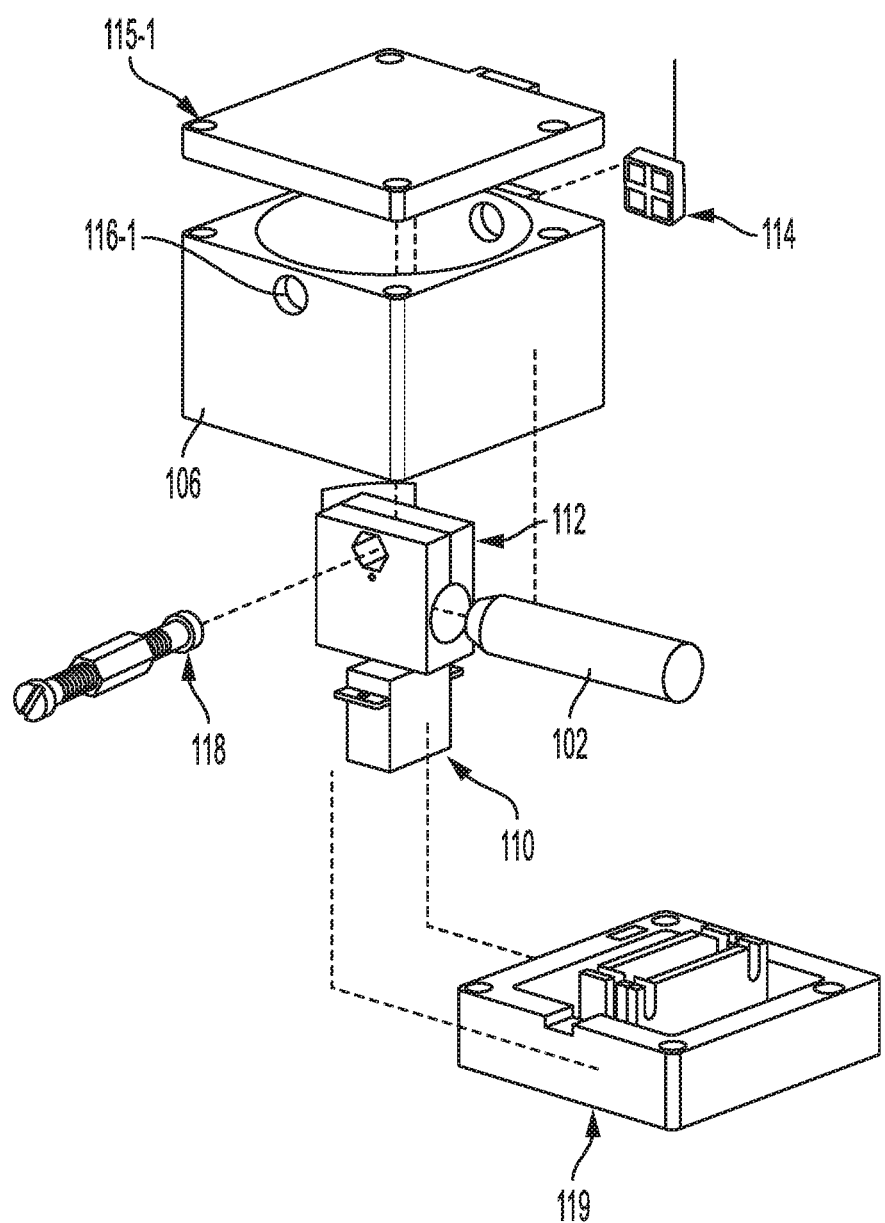
FIG. 3. shows an exploded view of one embodiment of the invention.

In addition, another, or the same, motor that moves the applicator 102 in the housing 106 can be used to open and close an orifice 116-1 to the housing 106. For example, as shown in FIG. 3, one or several arms 118 may be moved to cover the orifice(s) 116-1. These arms may be spring-loaded to maintain contact the orifice 116-1 or walls, no matter what position the motor is in. The arms 118 may have covers 120 affixed to their ends to expand the surface area they cover. These covers may be made of felt or some other material with a low friction coefficient to facilitate the motion of the arms.

Figure 4:
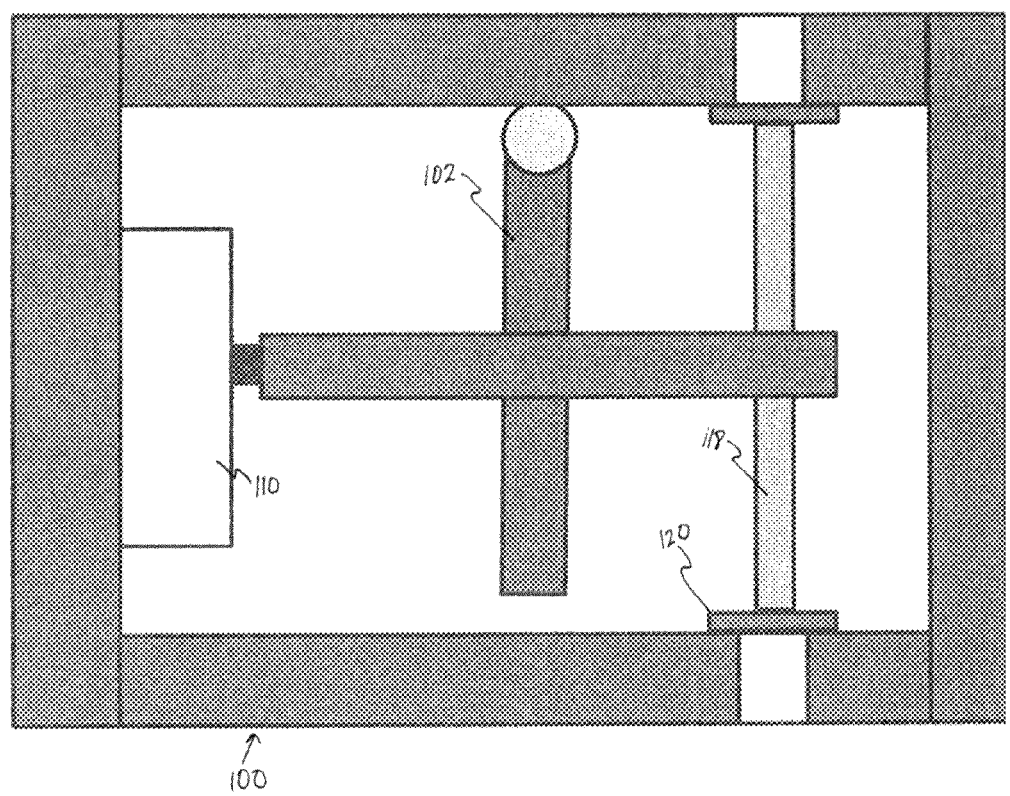
FIG. 4. shows a schematic view of one embodiment of the invention.
Figure 5:
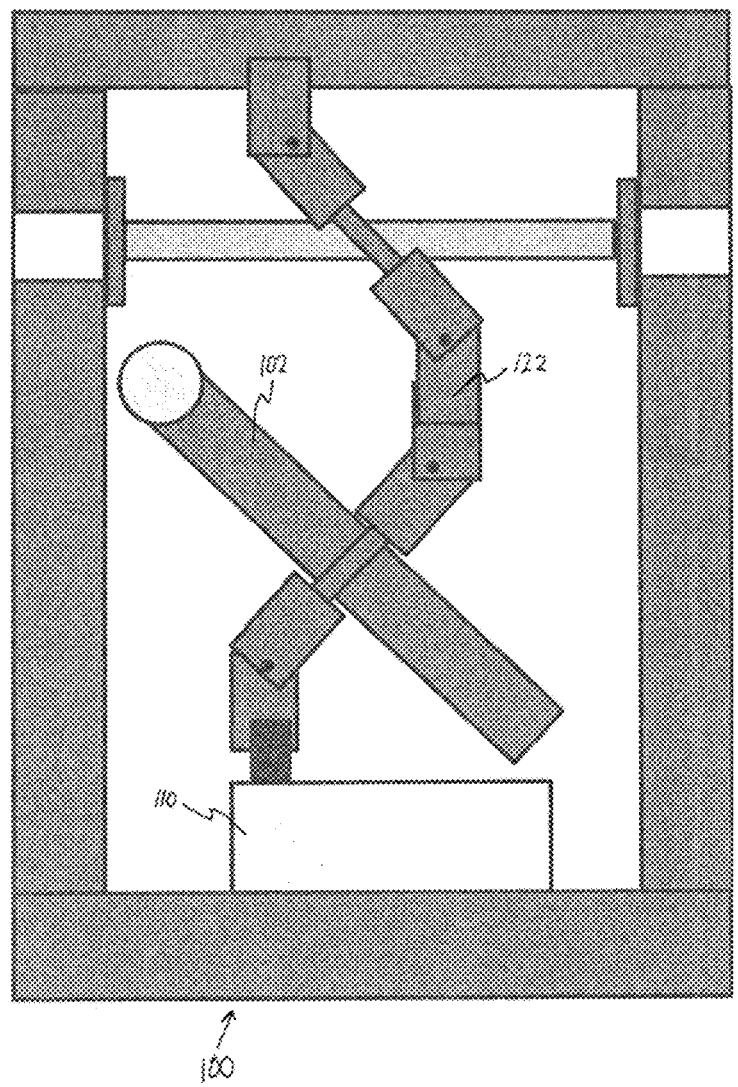
FIG. 5. shows a schematic view of one embodiment of the invention.

In the embodiment, as shown in FIG. 1, the applicator 102 is rotated in an arc parallel to the surface of the earth. In an alternative embodiment, the applicator 102 may be rotated in an arc perpendicular to the bottom 119 of the apparatus. This may be achieved by positioning the motor 110 on the wall of the applicator 102, or, alternatively, by rotating the entire apparatus on its side, as shown in FIG. 4. In yet an alternate embodiment, the motor 110 or the applicator 102 may be fixed at an acute angle relative to the bottom 119 of the apparatus. This will cause the applicator 102 to sweep in an arc oblique to the surface of the earth. In yet an another embodiment, as shown in FIG. 5, the applicator 102 may be affixed to a shaft 122 comprising a series of universal joints, arranged in a configuration such that the rotation of the shaft will cause the applicator 102 to rotate through an arc that is not parallel to the ground.

The motor system 110 can be activated by a microcontroller powered by a battery or a powered cable, or can be actuated manually by a spring- or other mechanical mechanism. The fan can also be controlled by the same microcontroller or be actuated manually. Furthermore, the apparatus may contain a resistive gas sensor, to detect the presence or concentration of the vapor. According to one embodiment, the microcontroller measures the current passing through the resistor to measure the concentration of the vapor in the apparatus. If the vapor is above or below a certain threshold the microcontroller may be programmed to either actuate, or cease actuating, the motor 110. In this way, the microcontroller may actively monitor the vapor concentration in the apparatus and adjust the vapor output accordingly. Because the sensor may be become coated in the liquid and cease to function properly, it may be desirable to occasionally heat the resistor to evaporate and liquid coating present on the sensor.

More than one of the boxes, consisting of an applicator 102 and a contact surface 108, can be connected to each other in a modular way to enable more than one liquid to be vaporized at a given time in proportion to each other depending on the amount of material spread on the internal contact surface 108 of the package. Such an array of devices could share one fan, or have individual fans.

A diagram of a non-limiting, illustrative embodiment of the invention is shown in FIG. 1. The liquid-containing applicator 102, in this case an applicator 102 can easily be removed/exchanged by a user as the liquid is dispensed onto the internal contact surface 108 by providing a clamp or other holding component within a applicator 104 of the package. The applicator 102 is positioned therein and rotated such that it moves over the internal contact surface 108. The temperature of the internal contact surface 108 can be controlled by internal heaters or coolers using peltier or resistive devices, for example. The internal contact surface 108 can be a cloth surface or other material surface with increased surface area for maximal absorption. The assembly with the surface 108 and the actuator and the bottle can be sealed in the chamber with a single or multiple orifices 116-1 that enable the vapor to be released from the chamber. The orifice 116-1 can be opened or closed by a separate motor, or by the same motor 110 using the applicator 102 as a valve to open or close the chamber. The bottle could be used to open and shut an orifice 116-1 by placing the bottle over it. A small fan can be incorporated in the chamber to pump air therethrough and accelerate the rate of vapor release.

Since the actuator assembly can be manually or electronically controlled, many different ways can be used to control the device. In the electronic control approach, buttons or dials on the front of the device can be used to rotate the motor 110, open the orifice 116-1, and control the fan at different speeds. If the device is powered by a cable connected to a computer, such as the USB bus, the computer can be used to control the motor 110 and the fan. Alternatively if the microcontroller has a RF interface, such as a bluetooth interface, for example, many handheld devices or computers can be used through apps to control the device. In addition, several of the delivery blocks can be stacked or placed near each other to be controlled by the devices. In the simplest embodiment, manual dials can be used to move the bottle within the chamber to apply the liquid and use diffusion. This approach will eliminate the use of electronics for reduced cost and simplicity.

The device 100 described above can also be incorporated with other functions to enable a multifunctional device. For example, a radio can be incorporated with or within the vapor-delivery box 100 that would allow one to listen to music with integrated aroma creating function that might correspond to specific song types. As a specific example, a morning alarm to wake up an individual can be enhanced by coffee aroma in the morning near the bedside.

The top of the device 115 may be modified to include a mobile device or computer charger. The top of the box can include a port onto which a cell phone can be mounted on and be charged, and still provide controlled aromas. Such a combined function may be very useful in personal office spaces where both functions of aroma control and cell-phone charging are required. These above examples are not meant to be limiting. The addition of an electronic or manual aroma delivery with other electronic or mobile applications would add aroma as an additional element of environmental control on specific timely manner without manual intervention.

Currently many products exist that measure quality of sleep at night time, usually by monitoring mechanical motion of the body using inertial sensors integrated within a body-mounted sensor unit. Using the aroma-therapy automatic delivery system, one can correlate the quality of sleep with different kinds of aromas being emitted near the bed of the person sleeping. Once these correlations are known, we can use the sensor data from the sleeping quality and dynamically control the quality of sleep by injecting different aroma combinations. As we know that the nose gets used to specific smells over time, the availability of dynamically altering the aroma content would keep the aroma sensation active.

Figure 6:
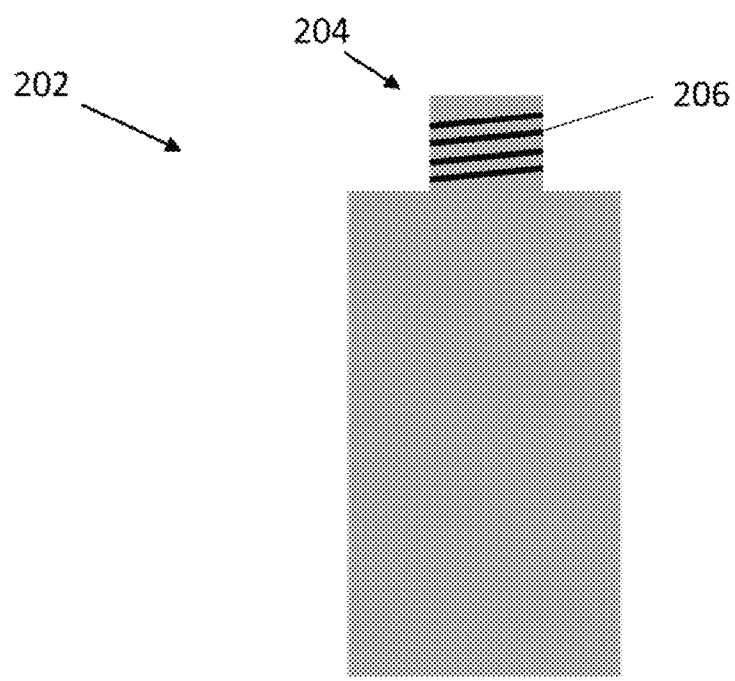
FIG. 6 shows a top view schematic representation of a bottle of an alternative embodiment of the vapor dispensing apparatus.

Referring now to FIGS. 6-18, there are shown various views schematic representations of a vapor dispensing apparatus 200 and its components, according to an alternative embodiment. The vapor dispensing apparatus 200 efficiently dispenses vapor through diffusion. Turning first to FIG. 6, there is shown a top view schematic representation of a bottle 202. The bottle 202 can be any container having an open end 204 with a connecting feature 206. In the embodiment depicted in FIG. 6, the connecting feature 206 is exterior threads. In an alternative embodiment, the connecting feature 206 is a friction fit tapered surface. The bottle 202 is sized and configured to contain liquid or fragrant evaporative material therein. In an embodiment, the bottle 202 comprises a volume of perfume therein.

Using the chamber 104 and housing 106 described above (in conjunction with FIGS. 1-5), the bottle 202 (replacing the applicator 102) containing the perfume is rotated and the open end 204 of the bottle 202 is in contact with the internal contact surface 108 (FIG. 1) to release the perfume by gravity when upside down. However, this requires the bottle 202 to be open end 204 (i.e., via open end 204) and will lead to diffusion out of the bottle 202 over time and could lead to unwanted dispersal if the entire apparatus 200, the enclosure (chamber 104 and housing 106 in FIG. 1) and the bottle 202, are turned upside down. Therefore, it would be beneficial to have a vapor dispensing apparatus 200 wherein the liquid is held within the bottle 202 with a seal that can be electronically actuated. Such a vapor dispensing apparatus 200 (and its component parts) is shown in FIGS. 6-18 and described in detail below.

Figure 7A:
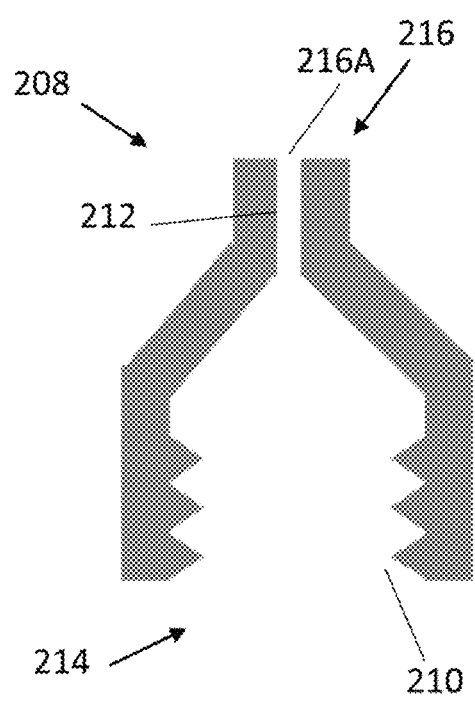
FIG. 7A shows a top view schematic representation of a cap of the alternative embodiment of the vapor dispensing apparatus.
Figure 7B:
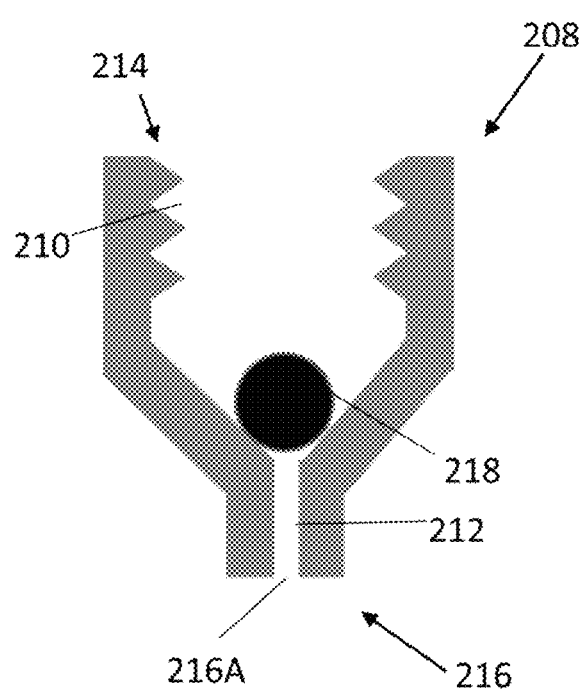
FIG. 7B shows the cap of FIG. 7A with a ball near or at a thin spout orifice.

Turning now to FIGS. 7A and 7B, there are shown top view schematic representations of a cap 208 for the vapor dispensing apparatus 200, according to an embodiment. The cap 208 is angled such that an inner volume 210 at a threaded end 214 is wider than an inner volume 212 at an open cap end 216. The threaded end 214 is configured to mate with the connecting feature 206 (e.g., exterior threads) on the bottle 202. The open cap end 216 comprises a thin spout orifice 216A for dispensing liquid. As shown in FIG. 7B, the cap 208 comprises a ball 218 therein to control the liquid flow from the cap 208. In the depicted embodiment, the ball 218 is adjacent to the thin spout orifice 216A. The ball 218 can be composed of any material that is resistant to degradation from liquid within the bottle 202, including iron and steel, for example.

Figure 8A:
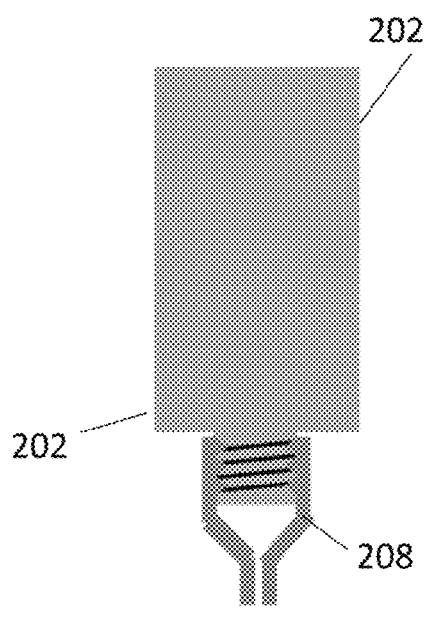
FIG. 8A shows a top view schematic representation of the cap attached to the bottle.
Figure 8B:
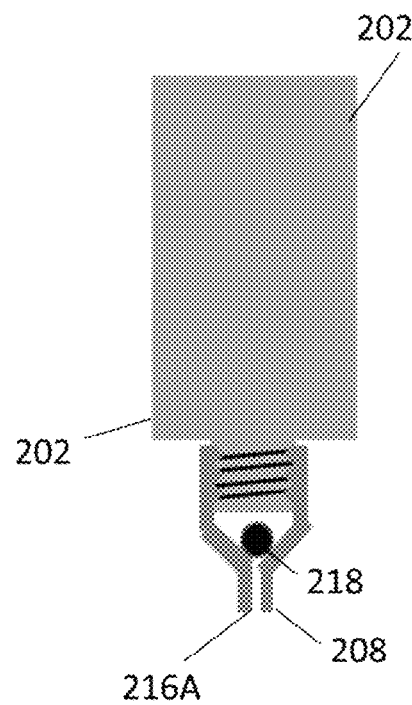
FIG. 8B shows the cap of FIG. 8A with a ball therein near or at the thin spout orifice.

Use of the ball 218 within the cap 208 is shown in conjunction with the bottle 202 in FIG. 8B, while the cap 208 is shown without the ball 218 in FIG. 8A. In FIG. 8A, the liquid in the bottle 202 can flow by itself without gating and perfume can leak through vaporization even when vertical. However, in FIG. 8B, the ball 218 prevents the liquid from exiting the bottle 202. In order to utilize the ball 218 to control liquid flow from the bottle 202, the ball 218 must be maintained in place over or near the thin spout orifice 216A.

Figure 9:
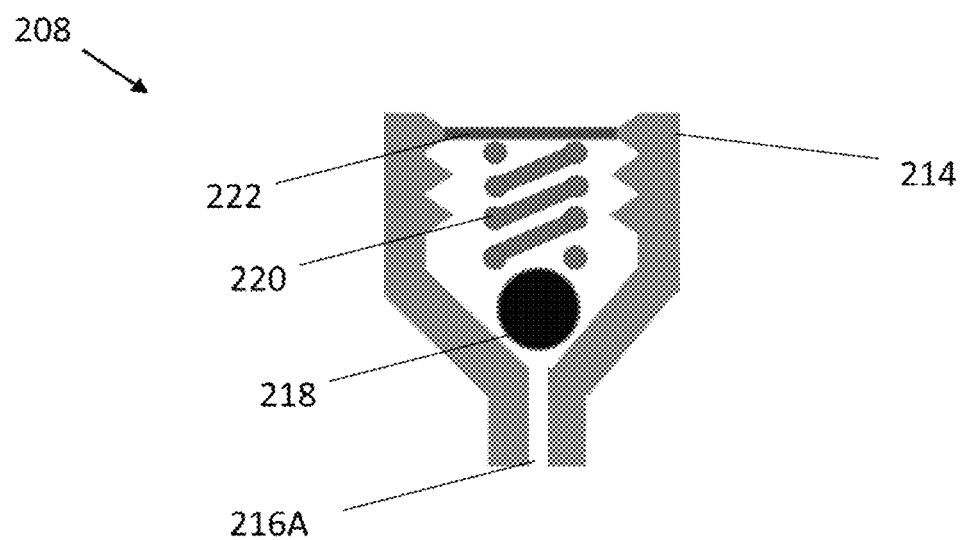
FIG. 9 shows a spring maintaining the ball in position within the cap.
Figure 10:
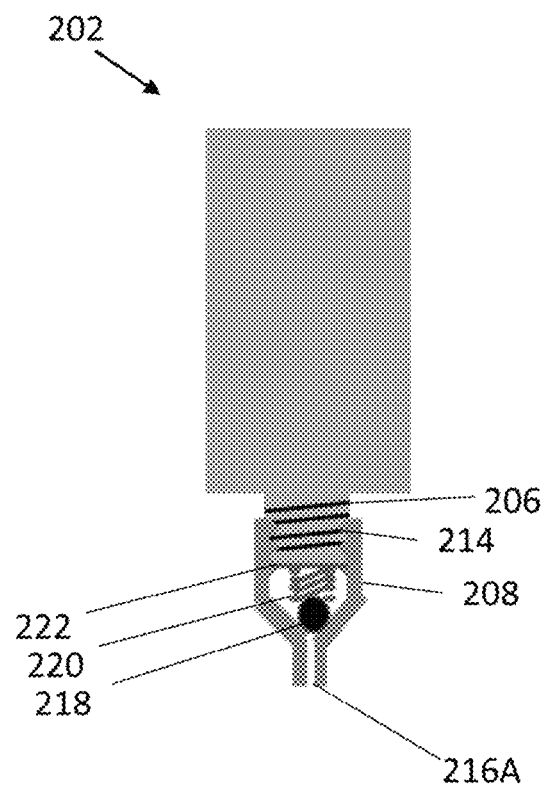
FIG. 10 shows the cap of FIG. 9 attached to the bottle.

In FIG. 9, a spring 220 and a retaining plate 222 are used to maintain positioning of the ball 218 over or near the thin spout orifice 216A. The spring 220 can be composed of plastic or any other like material. As shown, the retaining plate 222 extends across the threaded end 214 of the cap 208. The spring 220 extends from the retaining plate 222 and presses the ball 218 against the thin spout orifice 216A. Use of the spring 220 and retaining plate 222 within the cap 208 is shown in FIG. 10. The open end 204 of the bottle 202 is adjacent or presses against the retaining plate 222, as shown. The connecting feature 206 (e.g., exterior threads) of the bottle 202 can still mate with the threaded end 214 of the cap 208.

Figure 11:
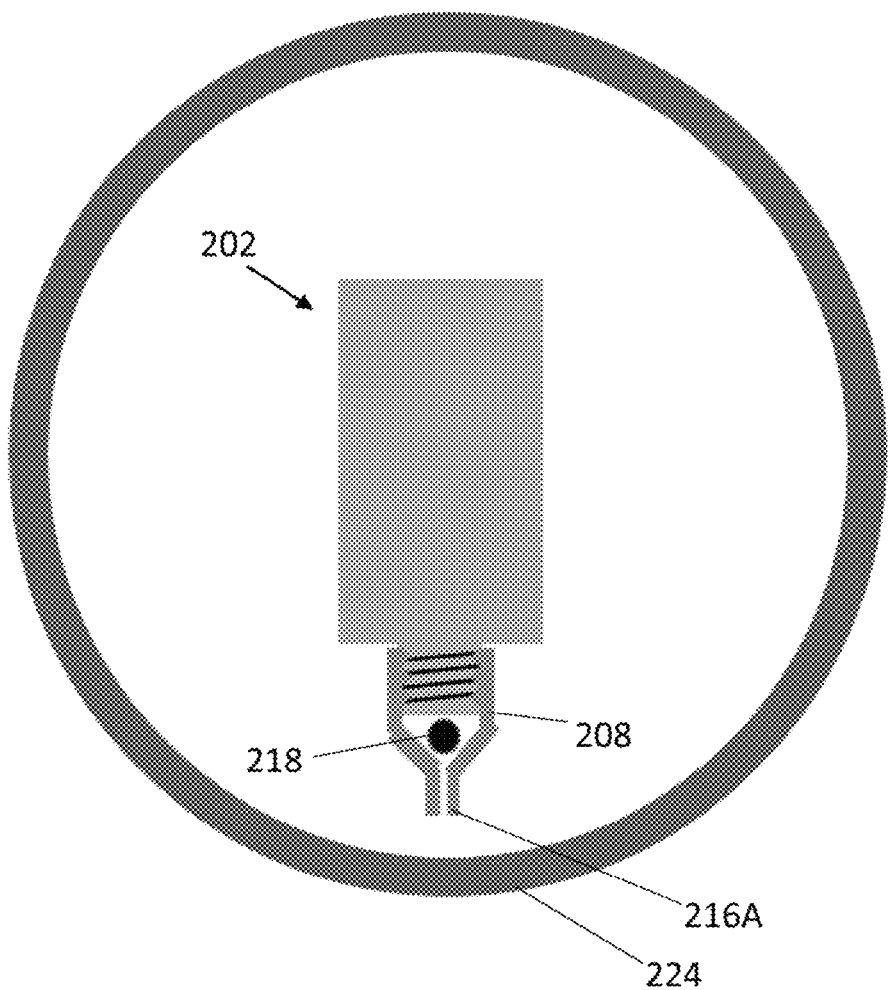
FIG. 11 shows a magnetic actuator extending around the bottle and cap in FIG. 10.
Figure 12:
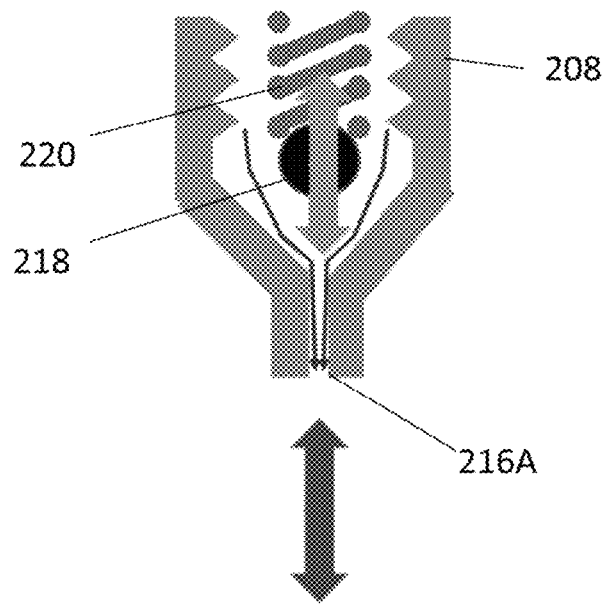
FIG. 12 shows the magnetic forces acting on the ball and spring within the cap.

Referring now to FIG. 11, there is shown a magnetic actuator 224 extending around the bottle 202 and cap 208 of the vapor dispensing device 200, according to an embodiment. In the embodiment shown in FIG. 11, the magnetic actuator 224 surrounds the bottle 202 and cap 208 in a circular fashion. In other words, the magnetic actuator 224 forms a circular perimeter around the bottle 202 and the cap 208. The magnetic actuator 224 induces a time varying magnetic field. The magnetic field moves the ball 218 up and down (away from and toward the thin spout orifice 216A) to create pressure and liquid motion to leak out from the cap 208, as shown in FIG. 12.

Figure 13:
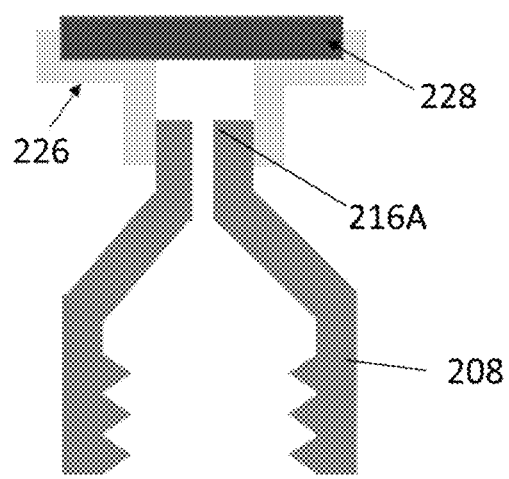
FIG. 13 shows a sponge retainer with a sponge attached to the cap.
Figure 14:
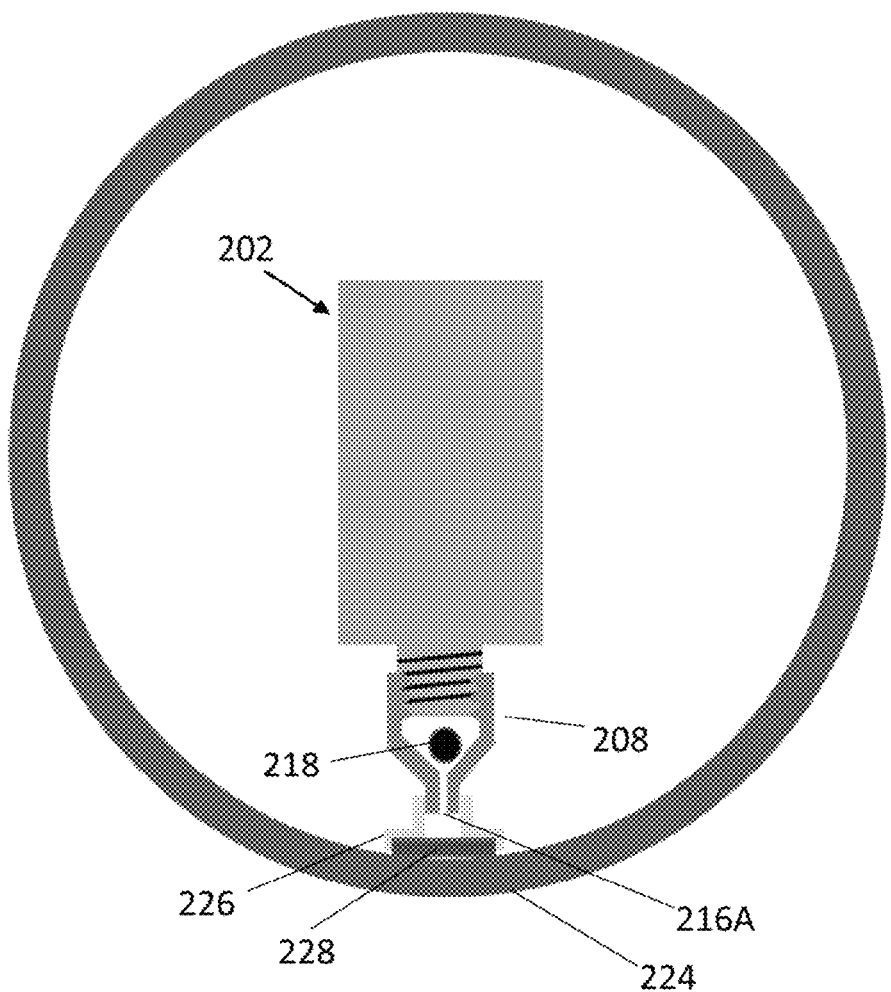
FIG. 14 shows the cap of FIG. 13 and bottle within the magnetic actuator.

Turning now to FIGS. 13 and 14, there are shown top views schematic representations of a sponge holder 226 and a sponge 228 used in conjunction with the cap 208 to provide an additional method for controlling liquid flow from the bottle 202. In the embodiment shown in FIG. 13, the sponge holder 226 is a device secured to or over the open cap end 216. The sponge holder 226 can have a friction or screw fit onto the open cap end 216. The sponge holder 226 contains a sponge 228 therein. The sponge 228 maintains perfume within its volume, but it can release liquid on a surface when moved and pressed (i.e., when pressure is applied thereto). As shown in FIG. 14, the sponge 228 is adjacent or extends along an interior (inner) surface 230 of the magnetic actuator 224.

Figure 15:
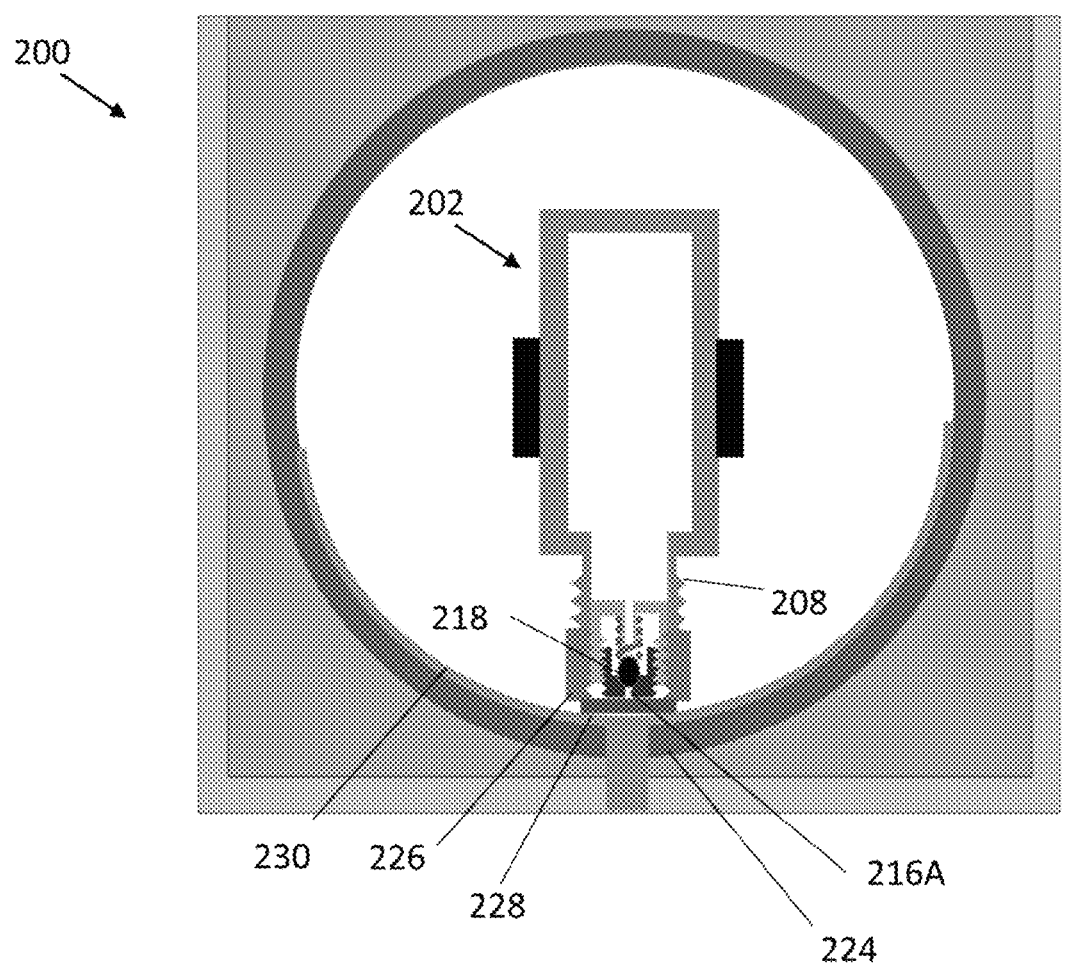
FIG. 15 shows a top view schematic representation of the vapor dispensing apparatus, according to an alternative embodiment.

An embodiment of the vapor dispensing apparatus 200 is shown in FIGS. 15-18. In FIG. 15, a user places the cap 208 on the bottle 202 such that the liquid can be extracted controllably using an external magnetic field source (i.e., magnetic actuator 224). This will enable a low-cost solution as a reusable bottle 202 can be used. The reusable bottle 202 consists of inexpensive components while the electronic control is in the body of the cassette holder. In some cases, to increase the rate at which the perfume is vaporized, the lining of the inner surface 230 can be heated to higher temperature. In this case, a heater from the package holding the cassette (holding the bottle 202) can be used to transfer heat through the cassette into the inner surface 230. The heat transfer from the external resistive heater can be transferred to a metallic thin layer on the inside of the inner surface 230 on which the liquid is rubbed (FIG. 15).

A bottle 202 can consist of a dispenser unit (DU) that contains a magnetic ball 218, which can be attracted using an external magnetic field. The ball 218 can be a small permanent magnet, perhaps coated with an inert material such as plastic such Teflon. The ball 218 can be also be made of iron-like material that can be attracted to an external magnetic field. Once an external magnetic field is applied, when the bottle 202 is upside down, the ball 218 will be displaced up and down due to the magnetic force. If the ball 218 is a permanent magnet, the external field will cause both attraction and repulsion causing the ball 218 to go up and down modulating the orifice opening 216A and liquid can leak out. If the ball 218 is made of a non-permanent magnet magnetic material (such as iron, nickel, or magnetic steel) each cycle of magnetic field actuation with attract the ball 218 towards the orifice. The pressing of the ball 218 towards the orifice and releasing can lead to excitation of a resonant mechanical motion such that liquid can be moved out.

Figure 16:
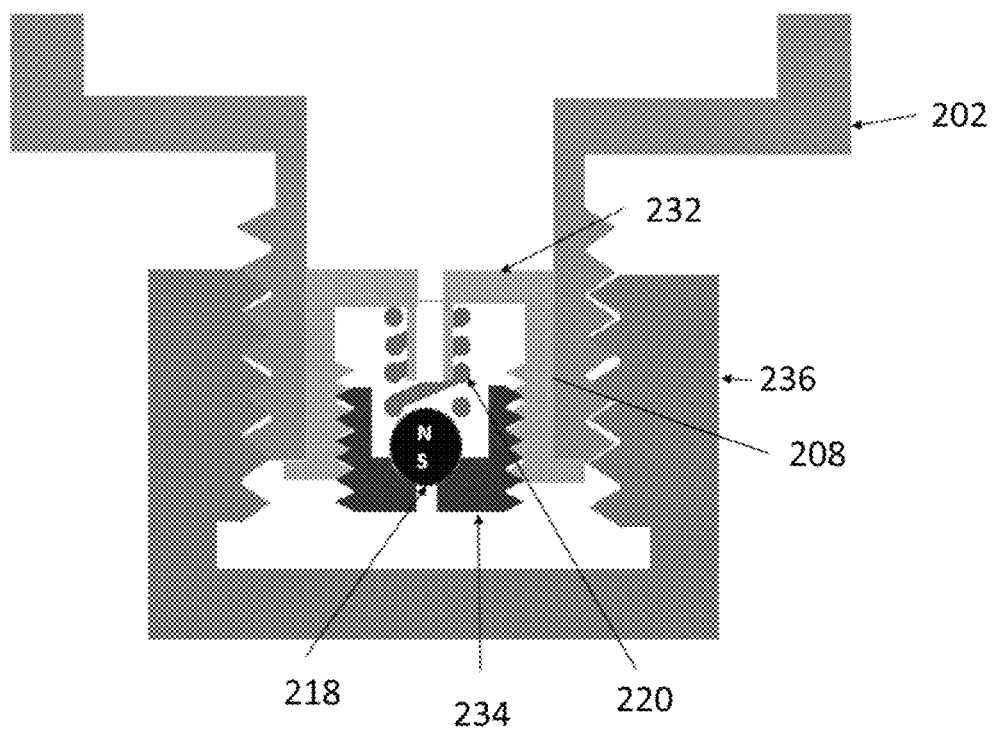
FIG. 16 shows a top view schematic representation of the cap of the vapor dispensing apparatus, according to an alternative embodiment.
Figure 17:
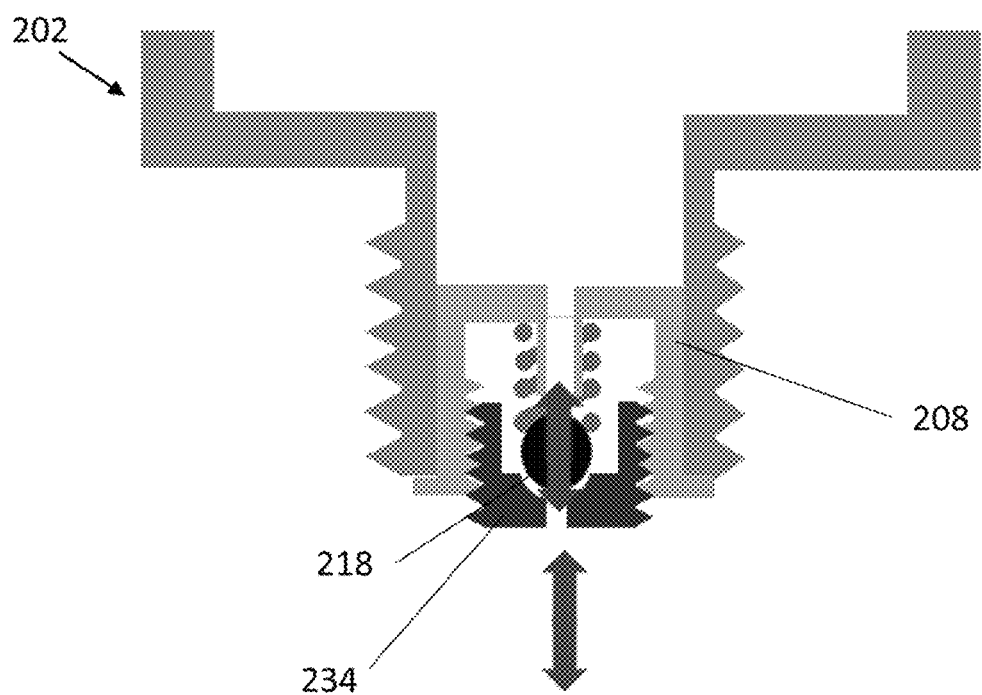
FIG. 17 shows another top view schematic representation of the cap of the vapor dispensing apparatus, according to an alternative embodiment.

The DU will be such that the ball 218 and spring 220 prevent liquid to leak out until magnetically actuated. As shown in FIG. 16, an insert 232 is placed with a tubular delivery pin in the center. The spring 220 is inserted so it hugs around the pin. The ball 218 is placed on a second screwed insert 234, or press fit insert, with the cavity for the ball 218 such that the ball 218 is pressed against the spring 220. An outer cap 236 is the cap that the user will remove before placing the bottle 202 inside the vapor delivery apparatus 200. The external magnetic field source 224 can be made of a coil that is driven by a current or can be a permanent magnet on a motor that rotates the magnet to change the external field. FIG. 17 shows how the magnet field can move the magnet and hence release the liquid around the ball 218.

Figure 18:
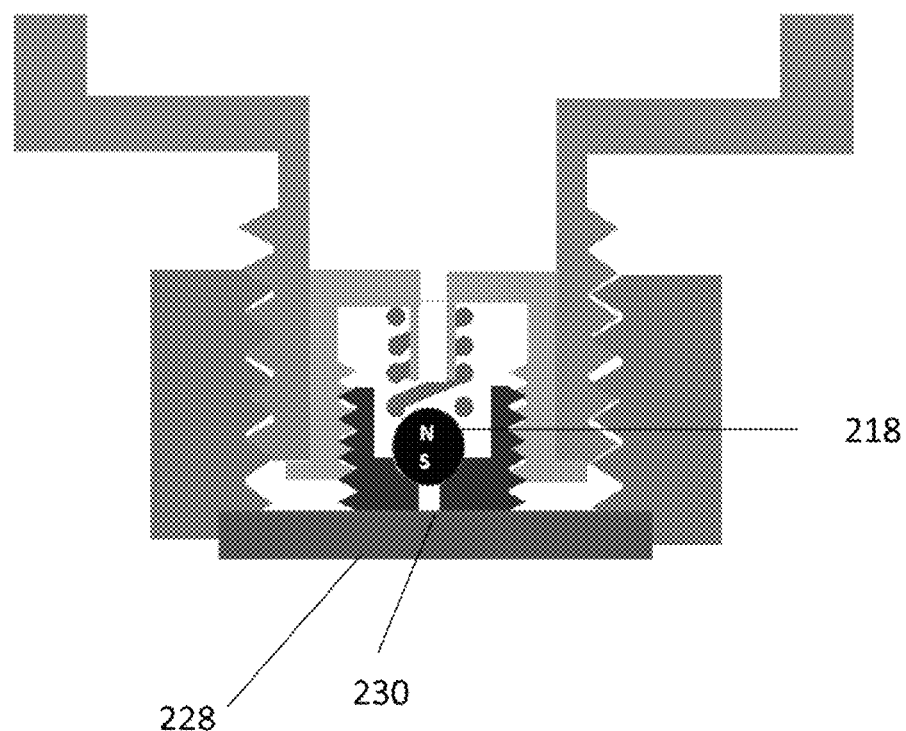
FIG. 18 shows yet another top view schematic representation of the cap of the vapor dispensing apparatus, according to an alternative embodiment.

In some cases, as mentioned above, it may be advantageous to place a spongy material 228 on the exit of the bottle orifice 216A as shown in FIG. 18. Instead of the droplet dropping on a specific site of the inner surface 230, it can first get inside a spongy material 228 that can then be place in contact with the inner surface 230. The surface area 230 of the applied perfume is increased to enable a higher rate of dispersal.

What is claimed is:

1. A vapor dispensing apparatus, comprising:
   a container having an open end with a cap removably attached thereto, the cap having an orifice;
   wherein the container is configured to store an evaporable material therein;
   a ball within the cap and adjacent the orifice;
   a spring extending from a first end of the cap toward the orifice;
   wherein the spring maintains the ball adjacent to the orifice;
   a magnetic actuator extending at least partially around the container; and
   wherein the ball is movable relative to the orifice based on magnetic force from the magnetic actuator.

2. The apparatus of claim 1, further comprising a sponge attached to an open cap end of the cap.

3. The apparatus of claim 2, further comprising a sponge retainer attached onto the open cap end, the sponge retainer having the sponge therein.

4. The apparatus of claim 1, wherein the evaporable material is fragrant.

5. The apparatus of claim 1, wherein the ball is composed of steel.

6. The apparatus of claim 1, wherein the ball is composed of iron.

7. The apparatus of claim 1, wherein the spring is composed of plastic.

8. The apparatus of claim 1, further comprising a connecting feature at the open end of the container.

9. The apparatus of claim 8, wherein the connecting feature is exterior threads.

* * * * *